United States Patent [19]

Ravaris

[11] Patent Number: 4,814,333
[45] Date of Patent: Mar. 21, 1989

[54] METHOD FOR TREATMENT OF HYPERCORTISOLEMIC, DEPRESSED PATIENTS

[75] Inventor: Charles L. Ravaris, Hanover, N.H.

[73] Assignee: The Trustees of Dartmouth College, Hanover, N.H.

[21] Appl. No.: 154,338

[22] Filed: Feb. 10, 1988

Related U.S. Application Data

[63] Continuation-in-part of Ser. No. 78,814, Jul. 28, 1987, abandoned.

[51] Int. Cl.$^4$ .......................................... A61K 31/495
[52] U.S. Cl. .................................................. 514/255
[58] Field of Search ........................................ 514/255

[56] References Cited

PUBLICATIONS

Chem. Abst. 97-207827y C1982.

Primary Examiner—Stanley J. Friedman
Attorney, Agent, or Firm—Hamilton, Brook, Smith & Reynolds

[57] ABSTRACT

Reduction of cortisol levels in depressed hypercortisolemic patients can alleviate depression. Cortisol levels can be reduced in these patients with drugs such as ketoconazole which block cortisol synthesis.

6 Claims, 2 Drawing Sheets

METHOD FOR TREATMENT OF HYPERCORTISOLEMIC, DEPRESSED PATIENTS

RELATED APPLICATIONS

This application is a continuation-in-part of application Ser. No. 078,814, filed July 28, 1987 abn.

BACKGROUND

During the past 40 years, clinicians interested in mood disorders have reported that a significant proportion of patients with endogenous depression also demonstrate a significant elevation in both plasma cortisol (hypercortisolemia) and in excretion of cortisol in the urine (hypercortisoluria). See Kathol, R. G., "Etiologic Implications of Corticosteriod Changes in Affective Disorder", *Psychiatric Medicine* 3, 135–162 (1985).

Moreover, these steroid changes appear to be related to the presence of active depression. That is, recovery from steroid abnormalities accompanies remission of the depressive symptoms. These, and other circumstances, has led to the supposition that corticosteroid changes are in some way related to the development of depression.

Cortisol is one of the adrenal cortical steroid hormones and these hormones are known to have significant effects on brain function and overall behavior. See McEwen, B. S., "Steroid Hormone Interactions with the Brain: Cellular and Molecular Aspects", *Rev. Neuroscience* 4, 1–30 (1979); Carpenter, W. T. and P. H. Gruen, *J. Clin. Psychopharmacol.* 2, 91–101 (1982).

Psychotic depressive episodes have been seen in patients with adrenal gland malfunctions such as Cushings Syndrome. See Kathol. R. G., *Psychiatric Medicine* 3, 135–162 (1985) for review. Moreover, mental disturbances sometimes occur in patients given cortisol. Clark, L. D. et al., *New Eng. J. Med.* 249, 178–183 (1953); Bunney, W. E. et al., *Am. J. Psychiatry* 122, 72–80 (1965).

The prevailing theory to explain these results is that a defect in the central nervous system (CNS) involving the hypothalamus-pituitary-adrenal gland (HPA) system causes cortisol hypersecretion in association with development of depressive symptoms. A controversy continues to exist, however, as to whether the hypercortisol secretion is primarily responsible for the observed psychopathology, or whether it is a secondary effect of the stress, weight loss, and altered sleep patterns of people with severe depression.

SUMMARY

This invention relates to a method of treating depression that is associated with hypercortisolemia. The invention is based on the discovery that a lowering of plasma cortisol levels in certain patients will alleviate depression.

The methods of this invention involve the administration to a depressed patient of a drug, or combination of drugs, which lower plasma cortisol levels by inhibiting the synthesis of cortisol in the patient's adrenal cortex. The effect of this lowering of plasma cortisol is an improvement in the symptoms associated with the affective disorder. In some embodiments of this invention, the method comprises administering a pharmaceutically effective amount of an imidazole drug that inhibits mitochondrial P-450 enzyme systems in the host's adrenal cortex. In other embodiments of this invention, the therapeutic method involves administering effective amounts of drugs capable of blocking 11-beta-hydroxylase cortisol synthesis. In preferred embodiments of this invention, the drug is ketoconazole. Ketoconazole blocks conversion of 11-deoxycortisol to cortisol in the adrenal cortex. Symptoms of depression are alleviated once cortisol biosynthesis is inhibited and plasma cortisol levels are reduced.

DETAILED DESCRIPTION OF THE INVENTION

This invention discloses a method of treating depression by reducing cortisol levels in the blood through the use of drugs that block cortisol biosynthesis. In particular, the methods of the present invention are useful in treating depressed patients who have excessive levels of plasma cortisol (hypercortisolemia). The methods of this invention are also used to treat patients with affective disorders such as severe and/or psychotic depression who also have hypercortisolemia. The methods are based on the discovery that the reduction of cortisol production results in an improvement of a patient's symptoms in cases of hypercortisolemia and clinical depression.

In general, methods of the present invention comprise the administration of drugs to clinically depressed patients with hypercortisolemia in amounts sufficient to lower plasma cortisol levels and alleviate clinical symptoms of the depression.

As used herein, the term "clinical or major depression" is used interchangeably with the terms "depression", "psychotic depression" and "affective disorder syndrome". These terms generally refer to development in a patient of psychic and somatic anxiety, social withdrawal, eccentric behavior, possibly loss of sense of identity, severe sleep disturbance, nihilistic delusions, hallucinations, etc. and may be accompanied by hypercortisolemia or hypercortisoluria.

Figure 1:
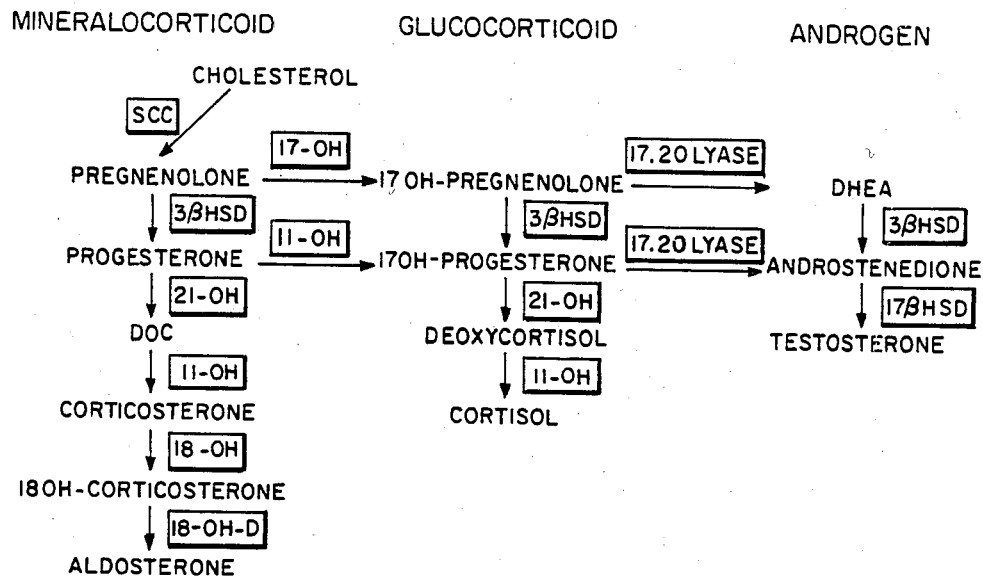
FIG. 1 shows the pathways of steroidogenesis in the adrenal gland. SCC: cholesterol side-chain cleavage enzyme; HSD: hydroxy steroid dehydrogenase; OH: hydroxylase; OH—D: hydroxy dehydrogenase.
Figure 2:
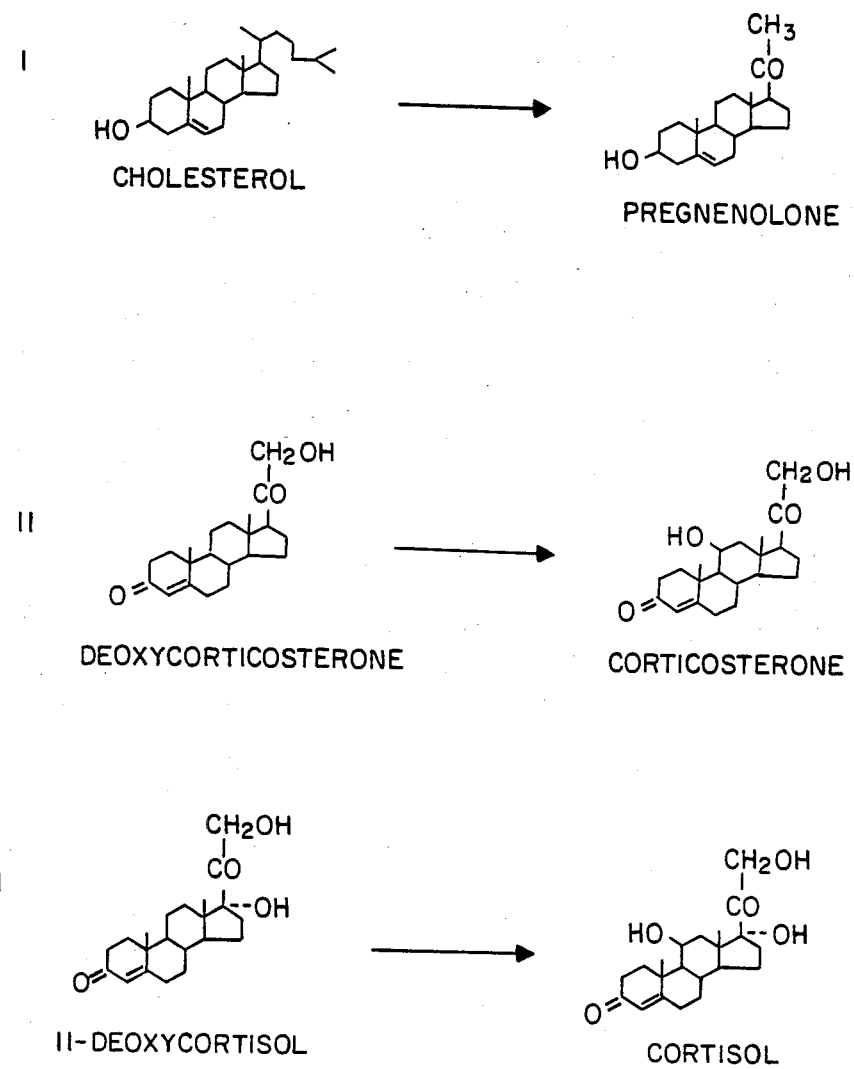
FIG. 2 shows chemical structures of the compounds involved in P-450 dependent mitochondrial enzyme reactions. Compounds (III) are those embodied in this invention.

In preferred embodiments of this invention, drugs are used to inhibit enzymes responsible for the conversion of 11-deoxycortisol to cortisol (FIG. 1). The chemical structures of these reactants are shown in FIG. 2. In preferred embodiments of this invention, imidazoles and compounds with imidazole or azole structures can be used to suppress cortisol synthesis. These imidazoles and imidazole analogs block mitochondrial P-450 enzymes in the adrenal gland, liver, testes and kidney. In particular, methods of this invention contemplate use of these drugs to block mitochondrial P-450 enzymes in the adrenal cortex. In so doing, a ferrihemochrome is formed by the binding of the nitrogen in the imidazole ring to the catalytic heme iron of the protophorphyrin moiety of the cytochrome P-450. This binding prevents oxygen binding to the enzyme and inhibits its activity.

Figure 3:
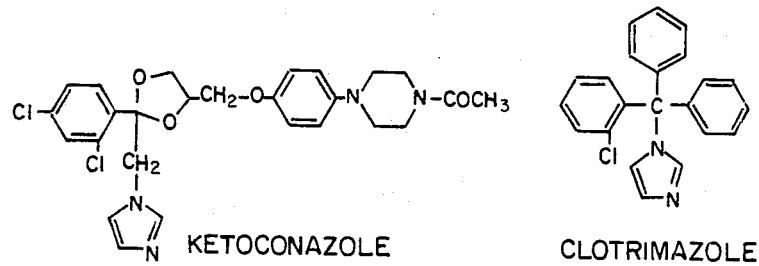
FIG. 3 shows chemical structures of P-450 enzyme inhibitors including the cortisol-synthesis inhibitors, ketoconazole and etomidate.
Figure 3:
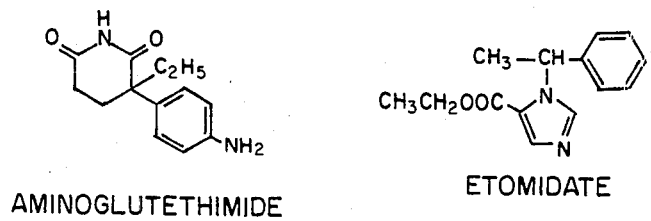

A variety of imidazole drugs are useful in embodiments of this invention. These drugs can be selected from the group consisting of ketoconazole, etomidate, clotrimazole, and aminoglutethimide (FIG. 3). In preferred embodiments of this invention, the drug ketoconazole is used to alleviate affective disorders in depressed patients and lower plasma concentrations of cortisol in these patients. Ketoconazole is a synthetic, broadspectrum antifungal agent (Janssen Pharmaceutica, Piscataway, N.J. 08854). It is cis-1-acetyl-4-[4-[[2-(2,4 dichlorophenyl)-2-(1H-imidazol-1-ylmethyl)-1,3 dioxolan-4-yl]methoxyl phenyl] piperazine and is known to be a potent inhibitor of adrenal steroid synthesis. For review see Oates, J. A. et al., *New England J. Med.* pp. 812–818 (Sept. 24, 1987).

The relationship of hypercortisolemia to observable psychopathology is still a matter of conjecture. That is, are the high cortisol levels a primary manifestation of depression (corticosteroid changes are the "cause" of depressive symptoms) or are the high cortisol levels a result of the weight loss, sleep deprivation and stress "caused" by depression?

The present invention avoids this conundrum with a direct demonstration that rapid and safe reductions in patient cortisol production are generated by administration of pharmaceutically effective levels of ketoconazole. Reductions in cortisol levels are accompanied by improvement in the patient's depressive illness.

In some embodiments of this invention, ketoconazole is given as a single daily dose of between about 200 mg to about 800 mg. The maximum recommended daily dose is 8 mg/kg of body weight. The therapeutic methods disclosed in this invention may include monitoring of the patient's cortisol blood and urine levels at the physician's discretion. The methods of the present invention include administration of steroid biosynthetic inhibitors in tablet form although aqueous solutions in suitable carriers may be used.

These imidazole derivatives, in particular ketoconazole, are almost insoluble in water, except at acid pH. Sufficient gastric acidity is required for complete dissolution and absorption so that methods of this invention required that the drug(s) be given after a meal.

One potential toxic reaction to the drugs used in this invention is alteration in liver function. See Oates, J. A. et al., Id. for review. Accordingly, methods described herein include liver function testing of the patient such as direct/indirect bilirubin and liver enzyme assays (SGGT, alkaline phosphatase, SGPT, SGOT). These tests can be determined prior to treatment and periodically for the first six to eight weeks of therapy. If there is a persistent elevation in these liver function tests and/or the patient develops jaundice, administration of the drug can be immediately stopped.

The invention is illustrated further by the following example.

EXAMPLE I

The following example illustrates the detailed use of ketoconazole in the successful treatment of hypercortisolemia and depression. It is a narrative of the history of a patient's admission, the laboratory investigation, the acute treatment and clinical outcome.

The patient was a 38 year old, white female, the mother of three children and recently separated from her husband. The patient told of an awareness of dysphoria at age 12 (menses onset at 11 years) and recurrent depression at her monthly premenstrual period. She experienced a post-partum depression with the birth of her second and third children. At age 33 years she was diagnosed with Cushing's Disease, a disorder resulting from increased adrenocortical secretion of cortisol. A pituitary adenoma was removed. At age 36, the depression recurred, followed by a recurrence of Cushing's Disease. The pituitary tumor was eradicated by proton beam ablation so that she is effectively hypophysectomized (e.g., without a functioning pituitary gland). The patient received appropriate hormone replacement therapy. In October 1986, the patient was hospitalized elsewhere for a psychotic depression without evidence of a recurrence of Cushing's Disease. Upon admission in April 1987, the patient demonstrated hysterical, regressive, and dependent personality traits. On Apr. 8, 1987, she was hospitalized on the Endocrinology Service at Dartmouth-Hitchcock Medical Center for reevaluation of recurrence of her Cushing's Disease (CD) and for depression. The physical stigmata of CD were absent. The magnetic resonance imaging (MRI) was negative for pituitary enlargement. However, on mental status examination, she was described as "labile affect, mood depressed, poor concentration, speech mildly pressured, thought content preoccupied with losses, fear of not knowing reality, loss of identity, sense of rejection, loss of self-esteem," and as "depressed, disorganized, and relates auditory and visual hallucinations" by the physician to whose service she had been assigned. She was seen by the Psychiatry consultation/liaison service and was diagnosed as being psychotically depressed. She was started on haloperidol (Haldol), 2 mg p.o. b.i.d., (with liquid, twice a day) and after three days lorazepam (Ativan), 1 mg p.o., t.i.d., (three times a day) was added. She responded to these medications with a "much improved mental status".

She was considered not to have a recurrence of her Cushing's Disease and was transferred to Psychiatry on 4/14/87 on the following medications: *1) Synthroid, 0.15 mg p.o. daily; Premarin, 0.125 mg p.o. daily; Calcium Carbonate, 650 mg tabs 2, p.o. t.i.d.; Flexoril, 10 mg p. o. t.i.d.; Haldol, 2 mg p.o. b.i.d.; and Ativan, 1 mg p.o. t.i.d. The two-day, low-dose Dexamethasone Suppression Test (DST) (0.5 mg q-6-hours×48 hours), with two separate 24-hour urine collections for urinary cortisol (normal range: 75–270 ug/24 hours) was performed. The pre-test urinary cortisol value was 379 ug/24 hours. The first 24-hour post-test value was 209 ug/24 hours; the second was 28 ug/24 hours. The control plasma cortisol at 8 am was 11.2 ug/dL; at 7 am, post 48-DST, it was 1.4 ug/dL. This data ruled out a recurrence of Cushing's Disease or of Cushing's Syndrome.

Determinations of adrenocorticotrophic hormone (ACTH) gave values of 12 and 20 pg/ml (expected adult values, 8 am to 10 am, <130 pg/ml. The TRH-TSH test showed a baseline TSH (thyroid stimulating hormone) of 0.2 u IU/ml (normal: 0.5–4.0 u IU/ml) and no increased secretion to the IV administration of 500 ug of TRH. This data suggested that the patient probably had some residual ACTH-producing tissue and that her replacement thyroid hormone (Synthroid; 0.15 mg p.o. daily) totally suppressed TSH secretion.

All psychotropic drugs were progressively discontinued. On admission to Endocrinology on 4/7/87, the plasma cortisol at 10 pm was 24.4 ug/dL (normal value <5 ug/dL) and prior to transfer to psychiatry on 4/13/87, the plasma cortisol (PC) at 11 pm continued high at 13.4 ug/dL. The 24-hour urine collection for cortisol, completed between 4/9–10/87 (volume 3650 ml; creatinine concentration, 47 mg/dL; creatinine/TV, 1.70 [normal range 0.8-1.9 grams/TV]) was 906 ug/24 hours (normal range 75-270 ug/24 hours). The patient continued to show the symptoms and signs of a major depression without psychotic features, notwithstanding the discontinuation of the haloperidol (Haldol) and the lorazepam (Ativan). Four weeks after her transfer to psychiatry, the patient persisted in showing a hypercortisolemia. On 5/12/87, the 7 am, 4 and 11 pm plasma cortisols were 38.2, 23.7, and 20.1 ug/dL respectively, and the urinary cortisol was 608 ug/24 hours.

On 5/19/87, after baseline videotape interview, the patient was started on 4 mg/kg of ketoconazole (patients weight=72 kg; dose=300 mg). The first dose of the drug reduced the urinary cortisol to 316 ug/24 hours, a 50 percent reduction. The patient said her mind felt "more clear" and she felt "less depressed". Within six days (5/25/87) and on 6 mg/kg ketoconazole daily (500 mg), the 24-hour urinary cortisol had dropped into the normal range, that is, 233 ug/24 hours. Within two weeks (6/2/87), and on the maximum doses given (8 mg/kg daily) (600 mg), the urinary cortisol bottomed out at 136 ug/24 hours (78 percent decrease). The patient was euthymic within 72 hours of the administration of ketoconazole and remained so over the next two weeks. The therapeutic change was documented by periodic repeats of the videotaped clinical interviews. To determine whether there was a relationship between the euthymia achieved and the administration of ketoconazole, with the patient's consent, the drug was discontinued on 6/6/87. After 72 hours, the urinary cortisol increased from 136 ug/24 hours to 235 ug/24 hours. Within six days (6/12/87), the urinary cortisol has risen to 288 ug/24 hours. The patient showed increased symptoms and signs of depression.

After a poor night of sleep, at 4 am, on 6/13/87, the patient awakened, demonstrated pressured speech, stripped her bed, packed her bags, and called her sister, who lived a two-hour drive from the hospital to come and fetch her promptly. The patient was interviewed at 9 am. The patient was in control, demonstrating neither depression nor mania. The decision was made not to restart the ketoconazole. By 12 noon, the patient was in a highly agitated state, saying she was very frightened and was "burning in Hell." She struck a nurse, breaking her glasses. She aggressively pulled the hair of a second nurse. She was placed in four-point restraint, crying and screaming loudly. Between 12 noon and 12 midnight on 6/13/87, the patient required haloperidol, 15 mg IM and 20 mg p.o. The ketoconazole was restarted with 600 mg given after supper. The haloperidol was continued at 5 mg p.o. t.i.d. and before sleep through Sunday, 6/14/87. A final dose of 5 mg was given at 8 am, Monday, 6/15/87, at which point haloperidol was discontinued. By Sunday, 6/14/87, the patient said she was "tired and sleepy". She was cognitively unimpaired and showed no psychotic symptoms. By Monday, 6/15/87, she felt remorseful about what she had done, believing she had injured and alienated the nursing staff and had frightened the other patients. She stated "I lost it, it was so terrible." During the day on Saturday, while she was psychotic and in restraints, the patient was incontinent of urine. Regrettably, with the turbulence her psychotic decompensation created, we did not obtain a 24-hour urine collection. The first post-psychotic urine sample obtained 72 hours later on 6/16/87 was normal at 152 ug/24 hours, down from 288 ug/24 hours. Over the next two weeks, that is from 6/16/87 to 6/30/87, the ketoconazole was reduced from 600 mg to 400 mg daily. The urinary cortisol dropped to a low of 40 ug/24 hours, well below the lower limit of normal (75 ug/24 hours). The patient complained of fatigue, sadness at her past behavior, but denied the symptoms and signs of depression. No psychotic symptoms recurred. The ketoconazole was reduced to 300 mg daily (4 mg/kg). The urinary cortisol rose to 95 ug/24 hours. The plasma cortisol was measured at 2300 hours on three successive occasions, namely 7/6, 7/7 and 7/8/87, with values of 6.5, 8.4 and 13.4 ug/dL. These three determinations preceded the patient's discharge to her home on 7/9/87. She was discharged on ketoconazole, 300 mg p.o. daily, after supper and Dalmane, 15 mg as needed for sleep. No other psychotropic medications were prescribed. Her hormone replacement therapy was as indicated previously. A summary of the salient dates, ketoconazole treatments, and urinary/plasma levels of ketoconazole is given in Table I.

TABLE I

Summary of Clinical Observations and Plasma/Urine Cortisol Concentrations

| Date (1987) | Dosage[a] | Cortisol Concentrations Urine[b] | Plasma[c] | Comments |
|---|---|---|---|---|
| April 7 | | | 24.4 | Admission |
| April 13 | | 906 | 13.4 | 11 p.m. |
| May 12 | | 608 | 38.2 | 7 a.m. |
| | | | 23.7 | 4 p.m. |
| | | | 20.1 | 11 p.m. |
| May 19 | 300 | 316 | | Ketoconazole started |
| May 25 | 500 | 233 | | |
| June 2 | 600 | 136 | | |
| June 6 | | 136 | | Treatment discontinued |
| June 9 | | 235 | | |
| June 12 | | 288 | | Signs of depression |
| June 13 | 600 | | | Ketoconazole started: psychotic episodes |
| June 16 | | 152 | | |
| June 30 | 400 | 40 | | No psychotic symptoms |
| July 6 | | | 6.5 | 11 p.m. |
| July 7 | | | 8.4 | 11 p.m. |
| July 8 | | | 13.4 | 11 p.m. |
| July 9 | | | | Discharged |

[a]Dosages in mg ketoconazole per day
[b]Urinary cortisol in ug/24 hr; normal range (75-270 ug/24 hr)
[c]Plasma cortisol in ug/dL;
normal range:
8 a.m. 4-19
6 p.m. 2-15
12 a.m. <5

This Example clearly demonstrates the following: (1) major depression with psychotic features precipitated by the hypercortisolemia and hypercortisoluria results from increased production of cortisol by the adrenal cortex; (2) ketoconazole can safely reduce the elevated cortisol levels, leading to the development in this patient of euthymia; and (3) since this largely hypophysectomized female had an elevation of cortisol leading to the development of her major depression with psychotic features, the elevated cortisol must be the result of a neurogenic, non-ACTH stimulating mechanism. Thus, it is possible that depression precipitated by hypercortisolemia may have a neurohormonal (ACTH) or a direct neurogenic basis. The final common pathway with either mechanism would be the synthesis of cortisol. Ketoconazole, by inhibiting this synthetic process, can be therapeutic notwithstanding the hormonal or neurogenic basis of the disorder.

The methods embodied in this invention demonstrate that it is possible to safely and predictably reduce the body's concentration of cortisol using the 11-beta-hydroxylase inhibitor, ketoconazole. Moreover, in a depressed patient, with progressive decrease and normalization of cortisol production, the depressive illness improves dramatically. Other depressed patients whose illness is associated with hypercortisolemia can potentially benefit by careful use of ketoconazole and other similar compounds to inhibit production of cortisol in the patient's body.

EQUIVALENTS

Those skilled in the art will recognize, or be able to ascertain, with no more than routine experimentation, many equivalents to the specific embodiments of the invention described herein. These equivalents are intended to be encompassed by the following claims.

I claim:

1. A method for treating a patient afflicted with mental depression associated with hypercortisolemia, comprising administering to the mentally depressed patient a drug which inhibits adrenal cortisol synthesis and lowers the blood level of cortisol in an amount effective to alleviate the depression.

2. A method of claim 1, wherein the drug inhibits adrenal 11-beta-hydroxylase activity.

3. A method of claim 2, wherein the drug is ketoconazole.

4. A method of claim 3, wherein the amount of ketoconazole administered is from about 200 mg to about 800 mg daily.

5. A method for treating patients afflicted with mental depression associated with hypercortisolemia comprising administering to the mentally depressed patient ketoconazole in an amount sufficient to alleviate depression.

6. A method of claim 1, wherein the drug which inhibits adrenal cortisol synthesis is selected from the group consisting of ketoconazole, etomidate, clotrimazole, aminoglutethimide and analogues thereof.

* * * * *